United States Patent [19]
Pfeiffer et al.

[11] Patent Number: 5,640,954
[45] Date of Patent: Jun. 24, 1997

[54] METHOD AND APPARATUS FOR CONTINUOUSLY MONITORING THE CONCENTRATION OF A METABOLYTE

[76] Inventors: Ernst Pfeiffer, Stauffenbergstr. 34, 89075 Ulm; Fabio Sternberg, Robert-Stolz-Str. 17, 89231 Neu-Ulm, both of Germany

[21] Appl. No.: 435,382

[22] Filed: May 5, 1995

[51] Int. Cl.⁶ ........................................... A61B 5/00
[52] U.S. Cl. ........................................ 128/635; 604/890.1
[58] Field of Search ............................ 128/632, 635; 604/890.1, 891.1, 31, 48, 45, 50, 51; 204/403, 415

[56] References Cited

U.S. PATENT DOCUMENTS

| | | | |
|---|---|---|---|
| 3,902,970 | 9/1975 | Levin | 204/403 |
| 4,633,878 | 1/1987 | Bombardieri | 128/635 |
| 4,671,288 | 6/1987 | Gough | 128/635 |
| 5,106,365 | 4/1992 | Hernandez | 128/632 |
| 5,109,850 | 5/1992 | Blanco et al. | 128/635 |
| 5,126,034 | 6/1992 | Carter et al. | 204/403 |
| 5,176,632 | 1/1993 | Bernardi | 128/635 |
| 5,193,545 | 3/1993 | Marsoner et al. | 128/635 |
| 5,298,022 | 3/1994 | Bernardi | 128/635 |

FOREIGN PATENT DOCUMENTS

| | | |
|---|---|---|
| 064369 | 11/1982 | European Pat. Off. . |
| 102458 | 3/1984 | European Pat. Off. . |
| 069247 | 10/1985 | European Pat. Off. . |
| 166920 | 1/1986 | European Pat. Off. . |
| 215678 | 3/1987 | European Pat. Off. . |
| 275390 | 7/1988 | European Pat. Off. . |
| 286118 | 10/1988 | European Pat. Off. . |
| 401179 | 12/1990 | European Pat. Off. . |
| 409467 | 1/1991 | European Pat. Off. . |
| 534074 | 3/1993 | European Pat. Off. . |
| 539625 | 5/1993 | European Pat. Off. . |
| 554955 | 8/1993 | European Pat. Off. . |
| 265001 | 2/1989 | German Dem. Rep. . |
| 3530689 | 3/1987 | Germany . |
| 3700119 | 7/1988 | Germany . |
| 4001760 | 8/1990 | Germany . |
| 3900119 | 8/1990 | Germany . |
| 4130742 | 3/1993 | Germany . |
| 4235768 | 5/1994 | Germany . |
| 1113744 | 9/1984 | U.S.S.R. . |
| 89/02720 | 4/1989 | WIPO . |
| 91/15993 | 10/1991 | WIPO . |

OTHER PUBLICATIONS

Schubert et al. "An Implantable Artifical Pancreas", Medical & Biological Engineering + Computing, vol. 18, No. 4, pp. 527–537, Jul. 1980.

K. Cammann: Das Arbeiten mit ionenselektiven Elektroden Springer–Verlag, Berlin Heidelberg New York 1977, pp. 100–106.

J. G. Schindler and M. V. Guelich: L–Lactat–Durchflusselektrode mit immobilisierter Lactat–Oxidase Fresenius Zeitschrift, Springer–Verlag 1981, pp. 434–436.

V.W. Mindt, et al.: Sensoren fuer Lactat und Glucose, Verlag Chemie GmbH, 1973, pp. 805–808.

P. Racine, et al.: An Instrument for the Rapid Determination of L–Lactate in Biological Fluids, Medical Instrumentation, vol. 9, No. 1, Jan.–Feb. 1975, pp. 11–14.

*Primary Examiner*—Angela D. Sykes
*Assistant Examiner*—Eric F. Winakur
*Attorney, Agent, or Firm*—Flynn, Thiel, Boutell & Tanis, P.C.

[57] ABSTRACT

The present invention is directed to a method and an apparatus for continuously monitoring the concentration of a metabolite, such as glucose or lactic acid, in biological tissue, in which a perfusion fluid is fed to a microdialysis probe implanted in the subcutaneous tissue and removed therefrom as dialysate after enrichment with the metabolites contained in the lymph. An enzyme is added to the dialysate and/or perfusion fluid, and the concentration of the metabolite in the dialysate is determined under the selective effect of the enzyme at a measuring point which is positioned ex vivo, using an electrochemical sensor. The enzyme is added to the dialysate in the form of a continuous enzyme solution flow upstream of the measuring point and in dependence of the throughput of the microdialysis probe.

28 Claims, 2 Drawing Sheets

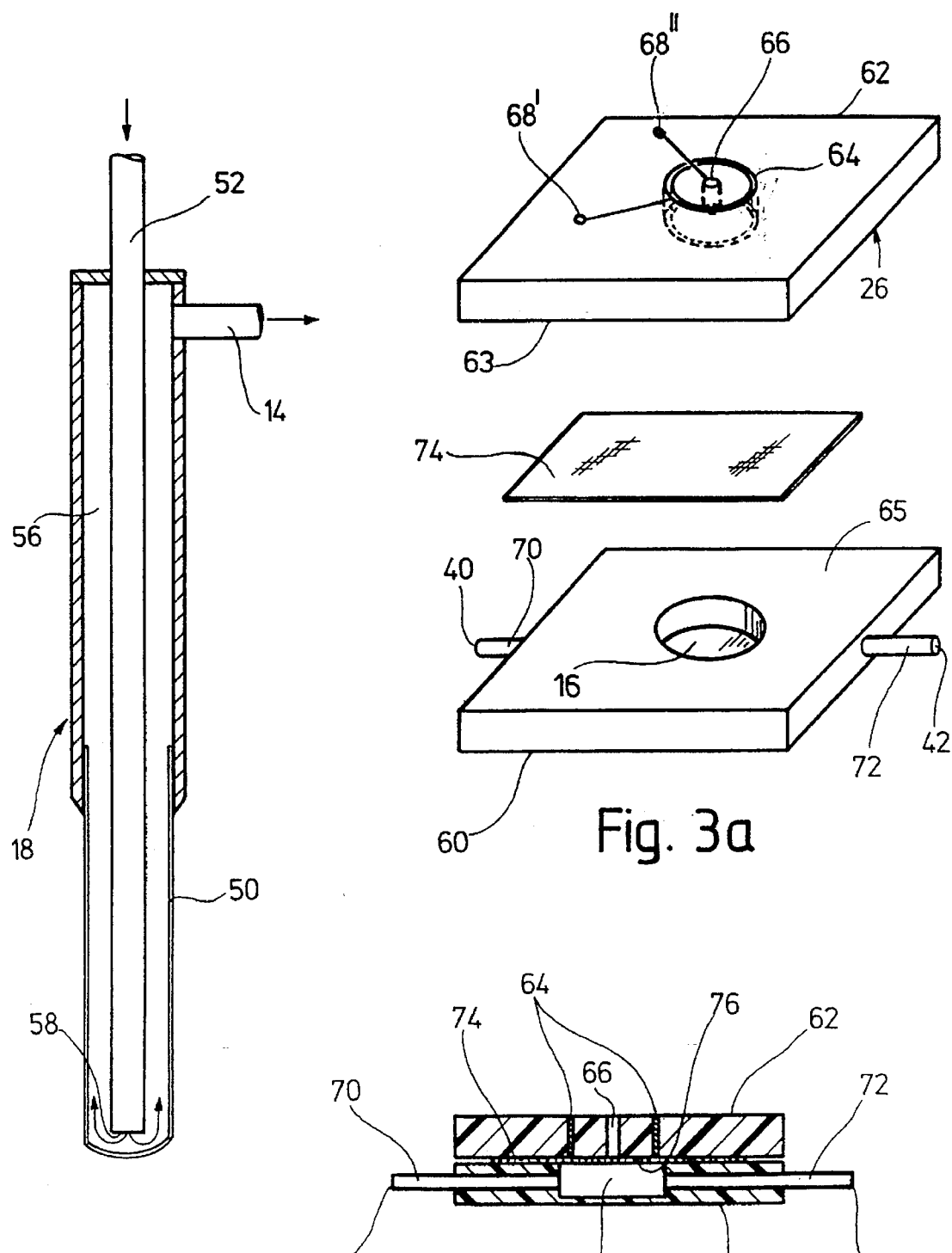

METHOD AND APPARATUS FOR CONTINUOUSLY MONITORING THE CONCENTRATION OF A METABOLYTE

BACKGROUND OF THE INVENTION

1. Field of the Invention

The present invention is directed to a method and an apparatus for continuously monitoring the concentration of a metabolite, such as glucose or lactic acid, in biological tissue, in which a perfusion fluid is fed to a microdialysis probe, preferably implantable in subcutaneous tissue, and removed therefrom as dialysate after enrichment with the metabolites contained in the lymph, in which an enzyme is added to the dialysate and/or perfusion fluid, and in which the concentration of the metabolite in the dialysate is determined under the selective effect of the enzyme at a measuring point, which is positioned ex vivo, using an electrochemical sensor.

2. Discussion of the Prior Art

Methods and apparatus of this type are primarily used in the field of human medicine. Apart from applications in sports medicine such as monitoring lactic acid during anaerobic strain or the determination of the variation of free fatty acids under different conditions, it is foremost the monitoring of glucose of diabetics which is of interest. Rapid information about the level of glucose in the blood is an essential condition for an effective and controlled administration of insulin. Under non-clinical conditions of everyday life, a self-monitoring of the glucose level by the patient using biosensors continually connected to the venous bloodstream is hardly possible, due, among other things, to problems of coagulation. The determination of the glucose concentration in the interstitial lymph, which is mostly linearly correlated to the glucose level in the blood, has proven to be a good alternative. In the earliest methods working with this principle (cf. EP-A 275 390), a needle sensor coated with an immobilized enzyme was introduced into the tissue and the glucose level was determined without taking samples in situ directly in the interstital fluid by measuring on an enzymatic-electrochemical basis. This concept proved to be disadvantageous, though, since the glucose sensitivity of the needle sensor continually decreased due to influences of physiological parameters during long-term measurements. In order to avoid this, it was proposed (DE-A-41 30 742) to extract metabolites from the lymph by means of a microdialysis technique, and to perform the actual measurement ex vivo, wherein transport of the samples from the subcutaneously implanted microdialysis probe to an electrochemical enzyme cell positioned outside the body is performed by way of a dialysate tube. When additionally rinsing the enzyme cell with a buffer fluid, this technique made it possible to diminish the influence of enzyme inhibitors present in the biological material and to improve the validity of long-term measurements. Intravenous reference measurements showed a high correlation and, under normal conditions, a small time delay between the glucose levels of blood and tissue. A drift of the measuring signal connected to the gradual loss of enzyme activity was observed, though. At the same time, the manufacturing and exchange of the enzyme-covered sensor caused comparatively high material expenditures.

In order to avoid these disadvantages, it was proposed in a method as described above (WO 89/027290) to add an enzyme to the dialysate and/or perfusion fluid flow, in order to guarantee a constant enzyme activity. In this, the enzyme is added to the perfusion fluid flow either as a slowly dissolving tablet or by diffusion through a hollow fibre. In this method of enzyme addition there is the danger, though, that the enzyme reaches the tissue of the patient, where it can lead to strong inflammation of the tissue. Furthermore, when there is a predetermined solubility profile of a tablet or a fixed diffusion rate through a hollow fibre, there is no possibility to adapt the concentration of the enzyme to different dialysate flows or to vary the concentration of the enzyme in a fixed dialysate flow.

OBJECT OF THE INVENTION

Based on these prior attempts, it is the object of the present invention to improve the known method and apparatus such that a controlled and, at any time, variable amount of enzyme may be added to the dialysate flow, and in which the patient must, under no circumstances, be endangered by the enzyme.

SUMMARY OF THE INVENTION

This object is solved by the combination of features recited in the present claims. Further advantageous embodiments and developments of the invention are given in the dependent claims.

The basic principle of the present invention is that the enzymatically catalyzed reactions should happen spatially removed from the sensor and with a continuous or occasional renewal of the enzyme. In this, the enzyme should under no circumstances find its way into the subcutaneous tissue, in order to ensure a high biocompatibility. It is thus suggested in the method according to the invention that the enzyme is added to the dialysate in the form of a continuous enzyme solution flow upstream of the measuring point and dependent on the throughput of the microdialysis probe.

The samples are passed along the sensor with a constant enzyme activity, and measurements in step with metabolic processes are possible in "real time" when the flow time may be disregarded. The concentration of the metabolite in the measuring dialysate flow is then advantageously determined by oxidizing the metabolite in the measuring dialysate by the action of the enzyme, and amperometrically determining the concentration of a reaction partner participating in or resulting from the oxidation reaction using two polarized electrodes of the sensor.

In order to protect the electrodes of the sensor from deposits and to separate the enzymatically induced processes from the electrochemical processes, the electrodes of the sensor are separated from the measuring dialysate by way of a protection membrane which is permeable for the reaction partner, preferably a dialysis membrane impermeable for the enzyme. In order to lower the costs, the protection membrane is advantageously provided to be exchangeable.

In the addition of the enzyme solution flow, depending on the throughput of the microdialysis probe, the ratio of the perfusion fluid flow to the enzyme solution flow should lie in the range of 1:10 to 10:1, and preferably be 1:1.

A sufficient enrichment of the perfusion fluid flow with the metabolite is obtained when the perfusion fluid flow rate is 0.1 to 15 µl/min, preferably 6 to 7 µl/min.

Depending on the application, the enzyme may be glucose oxidase (for determining glucose) or lactate oxidase (for determining lactate). Advantageously, the concentration of the enzyme in the enzyme solution is set to lie in the range of 100 U/ml to 10,000 U/ml.

A biocompatible perfusion fluid is, for instance, a physiological saline- or Ringer-solution, which may be buffered by phosphate in order to stabilize the pH-value. Furthermore, cresol may be added to the enzyme solution in a concentration ranging from 0.01 to 1 percent by weight in order to exclude possible bacteriological influences on the measurement.

In order to also ensure the linearity of the measurement at higher metabolite concentrations, the enzyme solution and/ or the perfusion fluid are enriched with oxygen, e.g. by subjecting these fluids to an oxygen atmosphere prior to the measurement.

In an apparatus for performing the method according to the invention it is suggested that the dialysate tube and/or the perfusion fluid tube be subjected to an enzyme solution taken from an enzyme solution reservoir. It is then possible to add the enzyme solution according to the requirements, and to use an inexpensive sensor which may be used with different enzymes.

According to an advantageous development of the invention, a feed channel is connected to the enzyme solution reservoir and merges with a measuring dialysate tube leading to the sensor together with the dialysate tube at a junction upstream from the sensor. By the mutual transport in the measuring dialysate tube, a sufficient interaction between the enzyme and the metabolite is ensured before the actual measurement. At the same time, the enzyme solution passing through the microdialysis probe is avoided, so that in the case of damage to the dialysis membrane no foreign protein passes through the microdialysis probe into the tissue.

A constant perfusion fluid flow may be produced by a first transport means which is positioned in the perfusion fluid tube and communicates with a perfusion fluid reservoir on the intake side and the microdialysis probe on the outlet side. Second transport means may be positioned downstream from the junction before or after the sensor, producing a constant measuring dialysate flow formed by the dialysate flow and the enzyme solution joining the dialysate flow at the junction.

A backflow of enzyme solution into the microdialysis probe is preferably prevented by making the capacity of the second transport means larger than the capacity of the first transport means, preferably twice as large.

In order to keep the perfusion fluid flow and the measuring dialysate flow exactly proportional to each other and, therefore, to ensure constant measuring conditions, the first and second transport means are designed to be metering pumps, preferably rolling pumps or piston pumps.

An especially compact set-up is attained by positioning the first and second transport means in the perfusion fluid and measuring dialysate tubes which are designed to be tubes of a single rolling pump compressible by a mutual roller. Different throughputs are realized by using tubes having different diameters.

In order to be able to establish quantitative proof of the metabolite in the measuring dialysate flow, a sensor suitable for amperometric measurements may be used, comprising a measuring electrode preferably consisting of gold or platinum and a comparative electrode preferably consisting of silver or stainless steel and positioned adjacent to the measuring electrode.

In order to separate the enzymatic processes from the electrochemical processes at the electrodes and to prevent deposits on the electrodes, it is an advantage when the sensor comprises a semipermeable protection membrane which separates the electrodes from the measuring dialysate flow and, preferably, is exchangeable.

In order to optimize the measuring conditions and to lower the signal drift, temperature control means regulating the temperature in the flow chamber to a preset value in the range of 20° C. to 35° C. may be provided. Alternatively, it is also possible to measure the temperature in the flow chamber and to compensate for the influence of the temperature on the signal by calculating a correction factor.

Backflow of enzyme-containing measuring dialysate in the direction of the microdialysis probe may be prevented by a self-locking check-valve positioned in the dialysate tube.

The sensor according to the invention is preferably used in combination with an advantageously portable measuring device comprising microprocessor-controlled analyzing electronics which record the signal of the sensor and generate therefrom digital data correlated with the concentration of the metabolite in the tissue.

The digital data aquired in this way may be stored in storage means at constant intervals in order to obtain a long-term overview. In order to inform the patient, the data may be displayed by display means, preferably a LCD-display.

The method and the apparatus according to the invention are advantageously used to compensate for diabetic defects in diabetic patients, wherein the insulin infusion is controlled according to the measured glucose level in the tissue of the patient.

BRIEF DESCRIPTION OF THE DRAWING

The invention is described in greater detail hereinafter with reference to an embodiment illustrated in the drawing, in which:

FIG. 2 shows a simplified section through a micordialysis probe;

FIGS. 3a and 3b show a sensor and a plate delimiting the flow chamber in an exploded view and assembled in a section view.

DETAILED DESCRIPTION OF THE DRAWING

Figure 1:
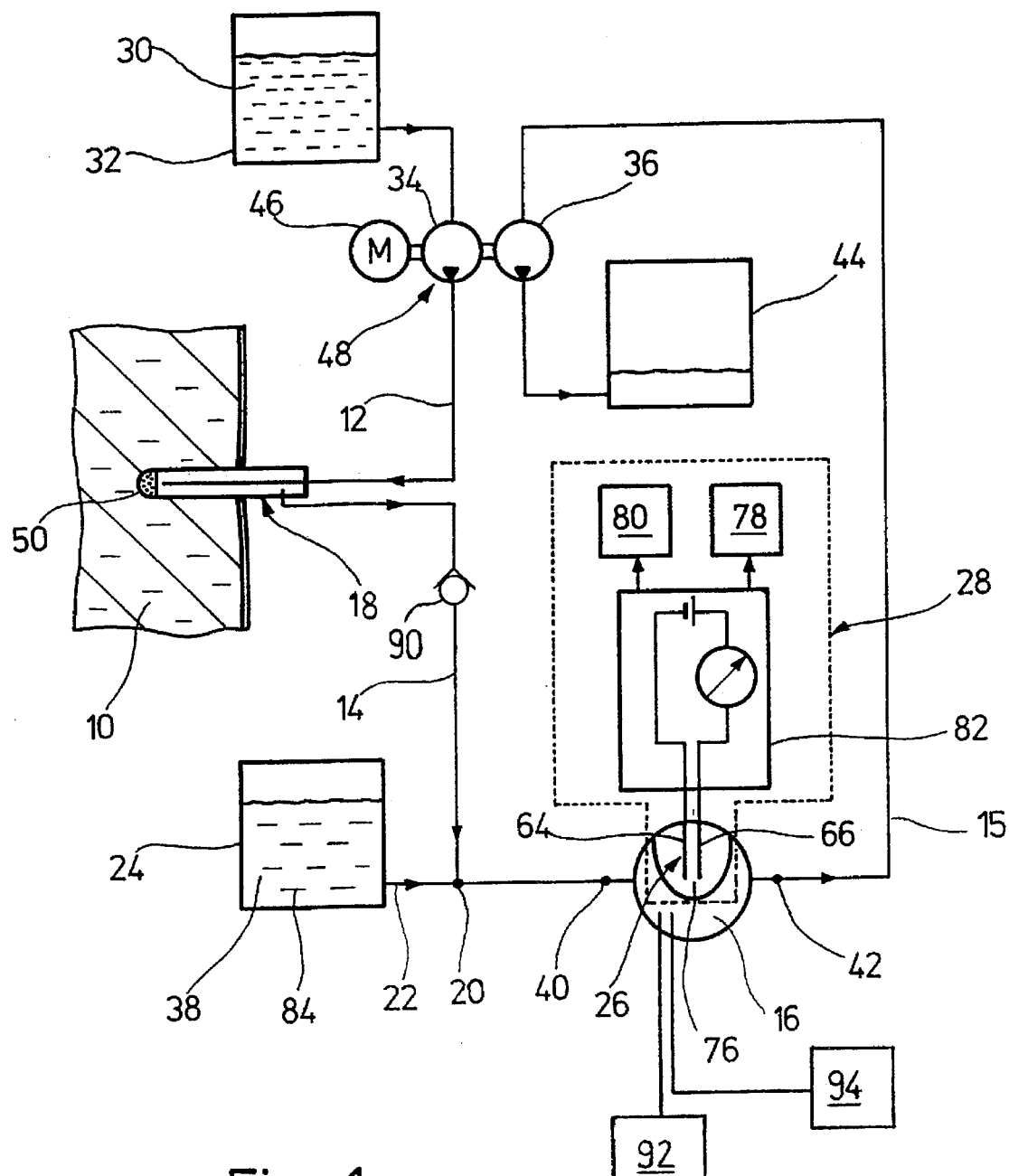
FIG. 1 shows a modular diagram of a measuring apparatus for monitoring metabolites in tissue.

The apparatus for monitoring metabolite concentrations in bodily tissue according to FIG. 1 consists primarily of a microdialysis probe 18 implanted into subcutaneous tissue 10 of a patient and a measuring device 28 positioned outside of the body, in which the microdialysis probe 18 subjected to a perfusion fluid flow at the inlet side by way of a perfusion fluid tube 12, communicates with a flow chamber 16 at the outlet side by way of a dialysate tube 14 and a measuring dialysate tube 15, a sensor 26 of the measuring device 28 is coupled to flow chamber 16, and in which a feed channel 22 of an enzyme solution reservoir 24 is connected inbetween dialysate tube 14 and measuring dialysate tube 15 at a junction 20. The perfusion fluid 30 consisting, e.g., of phosphate-buffered physiological saline solution or Ringer-solution is fed to the microdialysis probe 18 by way of first transport means 34 positioned in perfusion fluid tube 12 and fed from a perfusion fluid reservoir 32. Second transport means 36 positioned downstream from junction 20 and behind flow chamber 16 ensure, due to their larger capacity as compared to first transport means 34, that the perfusion fluid flow enriched with metabolites is removed from the microdialysis probe 18 and further transported as measuring dialysate flow through the measuring dialysate tube 15 with the addition of enzyme solution 38 at junction 20. In this, the higher capacity of second transport means 36 ensures that no enzyme solution 38 may flow from junction 20 in the direction of microdialysis probe 18. The measuring dialysate flow is led through the flow chamber 16 which is interconnected in the measuring dialysate tube 15 by way of junctions 40, 42, the measuring dialysate flow is led past sensor 26 and is finally led into a receptacle 44 which is positioned after second transport means 36 in order to be disposed of at a later time. First and second transport means 34, 36 may be designed as separate metering pumps or, as in the present embodiment, as tubes of a single rolling pump 48 which are compressible by a mutual roller which is advantageously driven by a battery powered motor 46. Rolling pump 48 acting on both perfusion fluid tube 12 and measuring dialysate tube 15 ensures, in a simple manner, the setting of a predetermined ratio of perfusion fluid flow to measuring dialysate flow according to the tube cross sections used. A check valve 90, which self-locks upon backflow of measuring dialysate in the direction of the microdialysis probe 18, is positioned in the dialysate tube 14.

As FIG. 2 shows, microdialysis probe 18 consists mainly of a double-lumen needle of approximately 20 gauge which is closed off at its proximal and distal ends and has a dialysis membrane 50 in the region of its distal end as well as a central inner hollow needle 52 which communicates with the perfusion fluid tube 12 and extends to the distal end. The dialysate tube 14 is also provided at the proximal end and extends by way of an annular channel 56 to the distal end of the needle and communicates there with the discharge opening 58 of the inner hollow needle 52. The membrane part 50 of the dialysis probe is fully embedded in the tissue after the implantation thereof and the porosity of the dialysis membrane 50 is such that the metabolic products to be measured, such as glucose or lactic acid, may diffuse through membrane 50 with hardly any resistance, while larger molecules are held back. For measuring glucose and lactic acid, the size of the pores is chosen to lie in the range of 0.01 to 0.03 μm. Due to the gradient in concentration with respect to the metabolite between the interstital fluid and the perfusion fluid pumped along the membrane 50, the perfusion fluid is loaded with metabolites from the intercellular tissue. This results in a dialysate, in which the concentration gradient is continually maintained by pumping away the dialysate.

The electrochemical sensor 26 shown in FIG. 3a, together with a chamber plate 60 defining flow chamber 16, has an isolator plate 62, into which a hollow-cylindric comparison electrode 64 made of silver or stainless steel, as well as a pin-shaped measuring electrode 66 made of platinum or gold, are embedded in a coaxial arrangement with respect to each other and protrude over the broad side surface 63 of isolator plate 62. The isolator plate further has two terminals 68', 68", each of which is connected in an electrically conducting manner to one of electrodes 64, 66 which are isolated with respect to each other. Chamber plate 60, which may be joined to the isolator plate, is provided with a cylindrical recess which has an open edge with respect to one broad side face 65 and is positioned in the centre of the plate, forming the flow chamber 16. Further, chamber plate 60 is penetrated by two connecting pipes 70, 72 which open into flow chamber 16 and protrude from opposite edges of the plate. Connecting pipes 70, 72 serve to connect flow chamber 16 to junctions 40, 42 of measuring dialysate tube 15. If the need arises, flow chamber 16 or the measuring dialysate flowing therethrough, may be kept at a predetermined temperature, e.g. in the range of 20° C. to 35° C., by temperature control means 92 or, alternatively, the temperature in flow chamber 16 is measured by temperature measuring means 94 and the effect on the signal is compensated by calculating a correction factor.

Isolator plate 62 and chamber plate 60 may, under mutual contact of their broad side faces 63 and 65, respectively, be connected to each other in a separable way by way of connecting means not shown. During assembly, a protection membrane 74 is clamped between chamber plate 60 and isolator plate 62, covering flow chamber 16 at its opening which faces electrodes 64, 66, membrane 74 preferably being a dialysis membrane (FIG. 3b). Protection membrane 74 may thus be easily exchanged when the need arises. In the assembled state, the active measuring area 76 of sensor 26 is located in the region between the faces of the electrodes covered by protection membrane 74. Comparison electrode 64 and measuring electrode 66 may be connected by way of their terminals 68', 68" to analyzing electronics 82 symbolically shown in FIG. 1, which have display means 78 and storage means 80, as described e.g. in EP-A-275 390, and may be subjected to a d.c. voltage.

During the measurement, the measuring dialysate passing sensor 26 in flow chamber 16 serves as an electrolyte. In the flow path between junction 20 and measuring area 76 an enzyme solution 38 added thereto and containing glucose oxidase as enzyme 84 causes the β-D-glucose extracted from the tissue to be oxidized to D-gluconolactone in the presence of oxygen and under liberation of $H_2O_2$. The D-gluconolactone hydrolytically reacts to D-gloconic acid in aqueous solution:

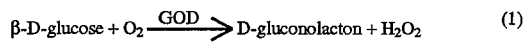

$$\beta\text{-D-glucose} + O_2 \xrightarrow{GOD} \text{D-gluconolacton} + H_2O_2 \quad (1)$$

The rate of formation of $H_2O_2$ can be measured amperometrically as a diffusion current at the platinum anode according to the following reaction:

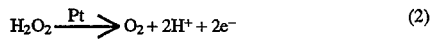

$$H_2O_2 \xrightarrow{Pt} O_2 + 2H^+ + 2e^- \quad (2)$$

The glucose concentration to be measured is proportional to the measured current. The oxygen contained in the measuring dialysate is sufficient to keep the reaction under way, particularly as the oxygen used in the glucose-conversion is recovered in the conversion of $H_2O_2$ at the platinum anode 66 and recirculated at least partially in the measuring dialysate. It is additionally possible, though, and advantageous especially at high concentrations of the metabolite, to enrich the enzyme solution 38 or the perfusion fluid 30 with oxygen.

For the determination of lactic acid, the basically same measuring setup may be used with an enzyme solution 38 which contains lactate oxidase as enzyme 84. Lactic acid contained in the measuring dialysate is then oxidized in the presence of oxygen in pyruvic acid under liberation of $H_2O_2$:

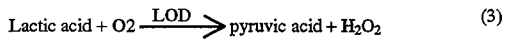

$$\text{Lactic acid} + O2 \xrightarrow{LOD} \text{pyruvic acid} + H_2O_2 \quad (3)$$

Here, too, the rate of formation of $H_2O_2$ may be measured by means of the electrochemical sensor as a diffusion current at the platinum anode 66 according to reaction (2).

The diffusion current is measured using a positive polarization voltage with the glucose sensor as well as with the lactic acid sensor.

It is basically possible to operate the sensor shown in FIG. 1 with a reversed bias, i.e. using the platinum pin 66 as, cathode and the cylindrical silver electrode 64 as an anode.

The oxygen contained in the measuring dialysate is reduced at measuring electrode 66 first to $H_2O_2$ and then to $H_2O$ according to the following reactions:

$$O_2 + 2H^+ + 2e^- \xrightarrow{Pt} H_2O_2 \quad (4a)$$

$$H_2O_2 + 2H^+ + 2e^- \xrightarrow{Pt} 2H_2O \quad (4b)$$

In order to measure the oxygen partial pressure in the measuring dialysate, the diffusion current at constant voltage between measuring cathode 66 and reference anode 64 is thus used as a measure for the number of $O_2$-molecules reaching the cathode per unit time.

In summary, the following may be said. The present invention is directed to a method and an apparatus for continuously monitoring the concentration of a metabolite, such as glucose or lactic acid, in biological tissue, in which a perfusion fluid is fed to a microdialysis probe 18, preferably implanted in subcutaneous tissue 10, and removed therefrom as dialysate after enrichment with the metabolites contained in the lymph, in which an enzyme 84 is added to the dialysate and/or perfusion fluid, and in which the concentration of the metabolite in the dialysate is determined under the selective effect of the enzyme 84 at a measuring point 76 which is positioned ex vivo, using an electrochemical sensor 26. The enzyme 84 is added to the dialysate in the form of a continuous enzyme solution flow upstream of the measuring point 76 and dependent on the throughput of the microdialysis probe 18.

We claim:

1. A method for continuously monitoring the concentration of a metabolite in biological tissue comprising the steps of:

implanting a microdialysis probe in subcutaneous tissue so that it contacts with lymph contained in the subcutaneous tissue;

feeding a perfusion liquid to the microdialysis probe whereby the perfusion liquid is enriched with the metabolite contained in the lymph;

removing the enriched perfusion liquid as a dialysate from the microdialysis probe;

adding an enzyme in the form of an enzyme solution continuously to the dialysate in an amount based on the flow rate of the dialysate to form a dialysate measurement solution;

determining the concentration of the metabolite in the dialysate by measuring the dialysate measurement solution ex vivo with an electrochemical sensor; and determining the concentration of the metabolite in the biological tissue based on the concentration of the metabolite in the dialysate.

2. The method of claim 1, wherein the metabolite in the measurement solution dialysate is oxidized by the action of the enzyme and the concentration of a reaction partner participating in or resulting from the oxidation of the metabolite is amperometrically determined by two polarized electrodes of the sensor.

3. The method of claim 2, further comprising the step of separating the electrodes of the sensor from the dialysate measurement solution by way of a removable dialysis membrane which is permeable to the reaction partner and impermeable to the enzyme.

4. The method of claim 1, wherein the ratio of the perfusion fluid flow rate to the enzyme solution flow rate lies in the range of 1:10 to 10:1.

5. The method of claim 4, wherein the ratio is 1:1.

6. The method of claim 1, wherein the perfusion fluid flow rate is 0.1 to 15 µl/min.

7. The method of claim 6, wherein the perfusion flow rate is from 6 to 7 µl/min.

8. The method of claim 1, wherein the enzyme is glucose oxidase or lactate oxidase.

9. The method of claim 6, wherein the concentration of the enzyme in the enzyme solution is in the range of 100 U/ml to 10,000 U/ml.

10. The method of claim 1, wherein the perfusion fluid is buffered by a phosphate and is a physiological saline- or Ringer-solution.

11. The method of claim 1, wherein cresol is added to the enzyme solution in a concentration ranging from 0.01 to 1 percent by weight.

12. The method of claim 1, wherein at least one of the enzyme solution and the perfusion liquid is enriched with oxygen.

13. An apparatus for continuously monitoring the concentration of a metabolite in biological tissue comprising a microdialysis probe for implantation in subcutaneous tissue; means for feeding a perfusion liquid to the microdialysis probe comprising a perfusion liquid reservoir, a first transport means for providing a flow of the perfusion liquid from the perfusion liquid reservoir to the microdialysis probe and a perfusion liquid tube for carrying the perfusion liquid from the first transport means to the microdialysis probe; a dialysate tube for removing a perfusion liquid enriched with the metabolite from the microdialysis probe; an enzyme solution reservoir containing an enzyme solution; a feed channel for carrying the enzyme solution to a junction formed by said feed channel and said dialysate tube where the enriched perfusion liquid and the enzyme solution are intermixed with each other to form a dialysate measurement solution; an ex vivo measuring device comprising a sensor for determining the concentration of the metabolite in the dialysate measurement solution, a second transport means for providing a constant flow of the dialysate measurement solution to the ex vivo measuring device and a dialysate measurement solution tube for carrying the dialysate measurement solution from the junction to the ex vivo measuring device.

14. The apparatus of claim 13, wherein the flow capacity of the second transport means is larger than the flow capacity of the first transport means.

15. The apparatus of claim 14, wherein the flow capacity of the second transport means is twice that of the first transport means.

16. The apparatus of claim 13, wherein the first and second transport means are metering pumps.

17. The apparatus of claim 16, wherein the metering pumps are rolling pumps or piston pumps.

18. The apparatus of claim 13, wherein the first and second transport means are positioned in the perfusion liquid and dialysate measurement solution tubes and are tubes of a single rolling pump which are compressed by a mutual roller.

19. The apparatus of claim 13, wherein the sensor extends into a flow chamber of the dialysate measurement solution tube and is designed for amperometric measurements, said sensor comprising a measuring electrode consisting of platinum or gold and a comparative electrode consisting of silver or stainless steel positioned adjacent to the measuring electrode.

20. The apparatus of claim 19, wherein the sensor additionally comprises a removable semipermeable protection membrane which separates the measuring and comparative electrodes from the dialysate measurement solution.

21. The apparatus of claim 19, wherein temperature control means regulate the temperature in the flow chamber to a preset value in the range of 20° C. to 35° C.

22. The apparatus of claim 19, wherein means are provided for measuring the temperature of at least one of the dialysate measurement solution and the flow chamber and for compensating for the effect of the temperature on a signal from the sensor by calculating a correction factor.

23. The apparatus of claim 13, wherein a check valve which self-locks upon backflow of the dialysate measurement solution in the direction of the microdialysis probe is positioned in the dialysate tube.

24. The apparatus of claim 13, wherein the measuring device is portable and comprises microprocessor-controlled analyzing electronics which record a signal from the sensor and generate therefrom digital data correlated with the concentration of the metabolite in the tissue.

25. The apparatus of claim 24, wherein the measuring device comprises storage means for storing the data at constant intervals and display means for displaying the data.

26. The apparatus of claim 25, wherein the display means is an LCD-display.

27. The apparatus according to claim 13, additionally comprising automatic insulin-infusion means for compensating diabetical defects in diabetic patients, wherein insulin infusion is controlled according to the measured glucose level in the tissue of the patient.

28. In a method for continuously monitoring the concentration of glucose in the tissue of a patient and compensating for diabetical defects in the patient by automatic insulin infusion means wherein insulin infusion is controlled according to the glucose level measured in the tissue of the patient, the improvement comprising the concentration of the glucose in the tissue of the patient being continuously monitored by a method comprising the steps of:

implanting a microdialysis probe in subcutaneous tissue of the patient so that it contacts with lymph contained in the subcutaneous tissue;

feeding a perfusion liquid to the microdialysis probe whereby the perfusion liquid is enriched with glucose contained in the lymph;

removing the enriched perfusion liquid as a dialysate from the microdialysis probe;

adding an enzyme in the form of an enzyme solution continuously to the dialysate in an amount based on the flow rate of the dialysate to form a dialysate measurement solution;

determining the concentration of the glucose in the dialysate by measuring the dialysate measurement solution ex vivo with an electrochemical sensor; and determining the concentration of the glucose in the tissue of the patient based on the concentration of the glucose in the dialysate.

* * * * *

UNITED STATES PATENT AND TRADEMARK OFFICE
CERTIFICATE OF CORRECTION

PATENT NO. : 5 640 954
DATED : June 24, 1997
INVENTOR(S) : Ernst PFEIFFER et al

It is certified that error appears in the above-indentified patent and that said Letters Patent is hereby corrected as shown below:

```
Column 8, line 8; change "method of claim 6" to
    ---method of claim 8---.
```

Signed and Sealed this

Twenty-first Day of October 1997

Attest:

BRUCE LEHMAN

Attesting Officer

Commissioner of Patents and Trademarks